United States Patent
Wang et al.

(10) Patent No.: US 10,081,599 B2
(45) Date of Patent: Sep. 25, 2018

(54) PREPARATION METHOD OF 4-(4-AMINO-3-FLUOROPHENOXY)-N-METHYLPYRIDINE-2-FORMAMIDE

(71) Applicant: Zhejiang Hisun Pharmaceutical Co., Ltd., Taizhou (CN)

(72) Inventors: Guan Wang, Taizhou (CN); Xufeng Yu, Taizhou (CN); Guo Wei, Taizhou (CN); Jian Chai, Taizhou (CN); Zhiqing Yang, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 15/532,374

(22) PCT Filed: Nov. 9, 2015

(86) PCT No.: PCT/CN2015/094108
§ 371 (c)(1),
(2) Date: Jun. 1, 2017

(87) PCT Pub. No.: WO2016/101714
PCT Pub. Date: Jun. 30, 2016

(65) Prior Publication Data
US 2017/0334856 A1    Nov. 23, 2017

(30) Foreign Application Priority Data

Dec. 24, 2014 (CN) .......................... 2014 1 0814308

(51) Int. Cl.
| | | |
|---|---|---|
| *C07D 213/81* | (2006.01) | |
| *C07D 213/127* | (2006.01) | |
| *C01D 1/04* | (2006.01) | |
| *B01D 9/00* | (2006.01) | |

(52) U.S. Cl.
CPC ......... *C07D 213/81* (2013.01); *B01D 9/0004* (2013.01); *C01D 1/04* (2013.01); *C07D 213/127* (2013.01)

(58) Field of Classification Search
None
See application file for complete search history.

(56) References Cited

U.S. PATENT DOCUMENTS

| 3,863,553 | A | 2/1975 | Koontz |
| 8,637,553 | B2 | 1/2014 | Boyer et al. |
| 9,072,796 | B2 | 7/2015 | Feng et al. |
| 2008/0090856 | A1 | 4/2008 | Flynn et al. |
| 2013/0012548 | A1 | 1/2013 | Xing et al. |

FOREIGN PATENT DOCUMENTS

| CN | 104250226 A | 12/2014 |
| WO | 2011113368 A1 | 9/2011 |
| WO | 2011113370 A1 | 9/2011 |

OTHER PUBLICATIONS

International Search Report for Application No. PCT/CN2015/094108 dated Jan. 19, 2016.

*Primary Examiner* — Zinna Northington Davis
(74) *Attorney, Agent, or Firm* — Lerner, David, Littenberg, Krumholz & Mentlik, LLP

(57) ABSTRACT

The present invention relates to a preparation method of 4-(4-amino-3-fluorophenoxy)-N-methylpyridine-2-formamide capable of enabling 4-chlorine-N-methylpyridine-2-formamide to react with 4-amino-3-fluorophenol in the presence of an inorganic base. The present invention employs the inorganic base to replace potassium t-butoxide in the prior art, thus effectively solving the problem of a potential safety hazard of the potassium t-butoxide in industrial production. In addition, after the reaction is completed, the present invention employs a crystallization method for separation to obtain a reaction product; thus compared with the methods of extraction, concentration and column isolation and purification employed in the prior art, the present invention has a simpler operation and a lower cost, results in less environment pollution and a higher yield, and is very suitable for industrial production.

17 Claims, No Drawings

PREPARATION METHOD OF 4-(4-AMINO-3-FLUOROPHENOXY)-N-METHYLPYRIDINE-2-FORMAMIDE

TECHNICAL FIELD

The present invention relates to the pharmaceutical field; specifically, it relates to a process for preparing a pharmaceutical intermediate, and more particularly, it relates to a process for preparing 4-(4-amino-3-fluorophenoxy)-N-methylpyridine-2-formamide.

BACKGROUND ART 4-(4-amino-3-fluorophenoxy)-N-methylpyridine-2-formamide is a pharmaceutical intermediate with the CAS no. 757251-39-1. Its structure is as follows:

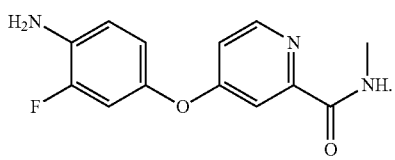 [SMILES: CNC(=O)c1cc(Oc2ccc(N)c(F)c2)ccn1]

4-(4-amino-3-fluorophenoxy)-N-methylpyridine-2-formamide is a key intermediate for the anticancer drug Regorafenib. There are generally two types of processes for its synthesis available in the prior art, which are as follows:

Method 1:

It has been reported in the U.S. Pat. No. 8,637,553B that 4-chloro-N-methylpyridine-2-formamide and 4-amino-3-fluorophenol are used as the starting materials to prepare 4-(4-amino-3-fluorophenoxy)-N-methylpyridine-2-formamide with N, N-dimethyl acetamide as the solvent and an organic base, potassium tert-butoxide, as the base. The reaction scheme was as follows:

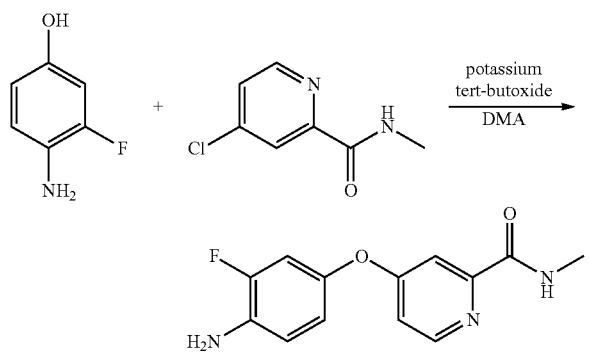

The foregoing process uses potassium tert-butoxide as the base in the reaction. As a result, it may easily explode in a large scale industrial production. Therefore, this process is associated with certain security risks. On the other hand, the after treatment of this process needs the processes of concentration, extraction and so on, which may cause great inconvenience in the industrial production and generate a lot of waste water. In particular, the reaction system of this process is in a dark black color, which makes it difficult to distinguish the boundaries between various extraction layers. Moreover, according to the patent disclosures, the highest yield of this process is 77%.

Method 2:

The U.S. Pat. No. 20080090856A reports that the amino group of 4-amino-3-fluorophenol is first protected with a ketone (for example, 2-methyl pentanone), and then it reacts with 4-chloro-N-methylpyridine-2-formamide in the presence of the organic base potassium tert-butoxide, and finally undergoes a de-protection step to prepare the target product, 4-(4-amino-3-fluorophenoxy)-N-methylpyridine-2-formamide. The reaction scheme was as follows:

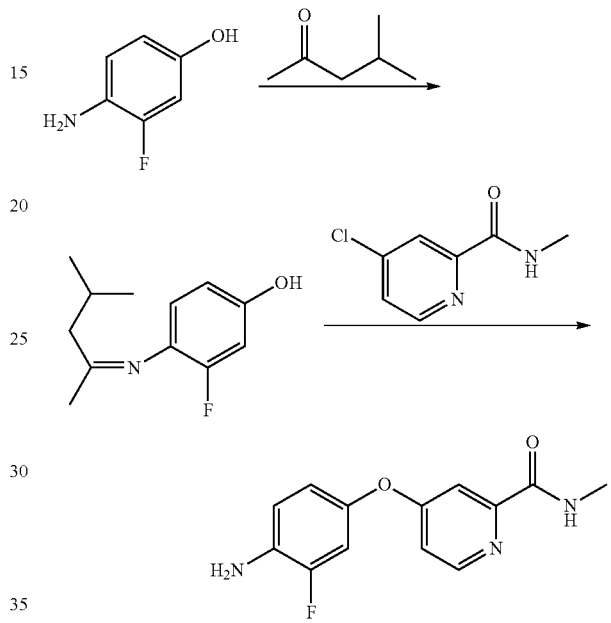

The foregoing process has additional steps of adding a protection group and then removing the protection group, which makes the preparation process more cumbersome, especially the second step reaction, which has a yield of merely about 78%.

In view of the various defects present in the synthesis of 4-(4-amino-3-fluorophenoxy)-N-methylpyridine-2-formamide disclosed in the prior art, providing a low cost and high yield synthesis route for 4-(4-amino-3-fluorophenoxy)-N-methylpyridine-2-formamide is an urgent problem need to be solved in order to achieve a large scale production of this pharmaceutical product.

SUMMARY OF THE INVENTION

The present invention provides a process for the preparation of 4-(4-amino-3-fluorophenoxy)-N-methylpyridine-2-formamide with low cost, high yield, simple operation and high safety, so as to overcome the defects in the prior art, including low yield, high cost, and having security risks, etc.

In order to solve the technical problems of the prior art mentioned above, the present invention employs the following technical solutions:

According to one aspect of the present invention, the present invention provides a process for preparing 4-(4-amino-3-fluorophenoxy)-N-methylpyridine-2-formamide shown in the formula below,

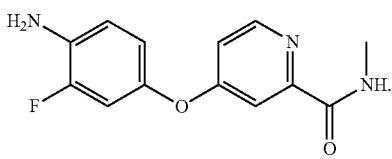

In one embodiment of the present invention, the preparation process comprises:
(a) under an inert gas atmosphere, in the presence of an inorganic base, reacting 4-chloro-N-methylpyridine-2-formamide shown in the formula below

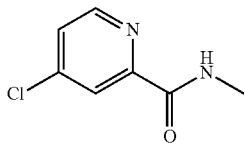

with 4-amino-3-fluorophenol shown in the formula below

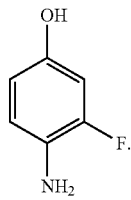

In one preferred embodiment of the present invention, the inorganic base is selected from sodium hydroxide and potassium hydroxide, and preferably sodium hydroxide.

In another preferred embodiment of the present invention, a ratio (that is, a molar ratio) of 4-chloro-N-methylpyridine-2-formamide, 4-amino-3-fluorophenol and the inorganic base is 1.0:0.9 to 1.5:0.9 to 1.5, and preferably 1.0:1.1 to 1.3:1.1 to 1.3.

In another preferred embodiment of the present invention, the reaction is carried out in an organic solvent. In addition, the organic solvent is selected from the group consisting of N, N-dimethyl acetamide, N, N-dimethyl formamide and N-methyl pyrrolidone, and preferably N, N-dimethyl acetamide.

In another preferred embodiment of the present invention, the reaction temperature of the reaction is from 40 to 160° C., preferably from 80 to 140° C., and more preferably from 90 to 110° C.

In another preferred embodiment of the present invention, the reaction time for the reaction is from 1 to 24 h, and preferably from 1 to 6 h.

In another embodiment of the present invention, the process further comprises: (b) after completion of the reaction, adding a suitable amount of water to the reaction solution obtained in step (a), and then cooling to a temperature from −20 to 20° C. for crystallization, so as to obtain 4-(4-amino-3-fluorophenoxy)-N-methylpyridine-2-formamide.

In another preferred embodiment of the present invention, in step (b), it has been cooled to a temperature from 0 to 10° C. for crystallization.

In another preferred embodiment of the present invention, a ratio by volume of the water added in step (b) to the reaction solution obtained in step (a) is 0.5 to 3:1, and preferably from 1 to 2:1.

According to another aspect of the present invention, the present invention further provides a process for preparing Regorafenib, characterized in that the process comprises:
(1) preparing 4-(4-amino-3-fluorophenoxy)-N-methylpyridine-2-formamide according to the process above;
(2) reacting the 4-(4-amino-3-fluorophenoxy)-N-methylpyridine-2-formamide obtained in step (1) with 4-chloro-3-(trifluoromethyl) phenyl isocyanate to obtain Regorafenib.

In one preferred embodiment of the present invention, step (2) is carried out in an inert organic solvent including, but not limited to, toluene, acetone, or a mixture thereof.

The present invention has the following advantages:

Compared with the prior art, the beneficial effect of the present invention is mainly embodied in the following aspects: in one aspect, the present invention uses an inorganic base, such as sodium hydroxide or potassium hydroxide, instead of potassium tert-butoxide used in the prior art to effectively solve the problem that potassium tert-butoxide is a potential safety risk in the industrial production. In another aspect of the present invention, when using the process provided in the present invention, the yield of the reaction can be as high as 88%. In addition, in the present invention, after the completion of the reaction, the reaction product is isolated by crystallization, which, when compared to the approaches adopted in the prior art, such as extraction, concentration, column separation and purification, etc., has the advantages of simple operation, low cost, little environmental contamination, and hence is suitable for industrial production.

DESCRIPTION OF THE EMBODIMENTS

The present invention will be described in further detail with reference to specific embodiments; however, the scope of the present invention is not limited thereto.

EXAMPLE 1

Under the protection of nitrogen, 127 g of 4-amino-3-fluorophenol, 170 g of 4-chloro-N-methylpyridine-2-formamide, and 170 ml of N, N-dimethyl acetamide are successively added to a reaction vessel, which are stirred to dissolve, and then 40 g of sodium hydroxide is added, the temperature is then raised to 80° C. for 24 hours; 510 ml of water is added, then cool the mixture to a temperature of −20° C. and stir at the foregoing temperature overnight for crystallization, and then filter and dry to obtain 211 g of a brown colored solid of 4-(4-amino-3-fluorophenoxy)-N-methylpyridine-2-formamide. HPLC content is 98.1%, mp: 141.6 to 142.3° C., yield 80.6%.

EXAMPLE 2

Under the protection of nitrogen, 190.5 g of 4-amino-3-fluorophenol, 170 g of 4-chloro-N-methylpyridine-2-formamide, and 5100 ml of N, N-dimethyl formamide are successively added to a reaction vessel, which are stirred to dissolve, and then 84 g of potassium hydroxide is added, the temperature is then raised to 140° C. for 1 hour; 2550 ml of water is added, then cool the mixture to a temperature of 0° C., and stir at the foregoing temperature overnight for crystallization, and then filter and dry to obtain 213 g of a brown colored solid of 4-(4-amino-3-fluorophenoxy)-N-methylpyridine-2-formamide. HPLC content is 98.5%, mp: 141.6 to 142.4° C., yield 81.3%.

EXAMPLE 3

Under the protection of nitrogen, 165 g of 4-amino-3-fluorophenol, 170 g of 4-chloro-N-methylpyridine-2-formamide, and 1700 ml of N-methyl pyrrolidone are successively added to a reaction vessel, which are stirred to dissolve, and then 52 g of sodium hydroxide is added, the temperature is then raised to 100° C. for 6 hours; 1700 ml of water is added, then cool the resulting mixture to a temperature of 20° C., and stir at the foregoing temperature overnight for crystallization, and then filter and dry to obtain 222 g of a brown colored solid of 4-(4-amino-3-fluorophenoxy)-N-methylpyridine-2-formamide. HPLC content is 99.1%, mp: 141.5 to 142.5° C., yield 85%.

EXAMPLE 4

Under the protection of nitrogen, 165 g of 4-amino-3-fluorophenol, 170 g of 4-chloro-N-methylpyridine-2-formamide, and 1700 ml of N, N-dimethyl acetamide are successively added to a reaction vessel, which are stirred to dissolve, and then 52 g of sodium hydroxide is added, the temperature is then raised to 100° C. for 3 hours; 1700 ml of water is added, then cool the mixture to a temperature of 10° C., and stir at the foregoing temperature overnight for crystallization, and then filter and dry to obtain 232 g of a brown colored solid of 4-(4-amino-3-fluorophenoxy)-N-methylpyridine-2-formamide. HPLC content is 99.2%, mp: 141.5 to 142.5° C., yield 88.6%.

EXAMPLE 5

Under the protection of nitrogen, 297 g of 4-amino-3-fluorophenol, 306 g of 4-chloro-N-methylpyridine-2-formamide, and 3060 ml of N, N-dimethyl acetamide are successively added to a reaction vessel, which are stirred to dissolve, and then 100 g of sodium hydroxide is added, the temperature is then raised to 100° C. for 2 hours; 3400 ml of water is added, then cool the mixture to a temperature of 10° C., and stir at the foregoing temperature overnight for crystallization, and then filter and dry to obtain 414 g of a brown colored solid of 4-(4-amino-3-fluorophenoxy)-N-methylpyridine-2-formamide. HPLC content is 99.5%, mp: 141.5 to 142.5° C., yield 88.4%.

EXAMPLE 6

Under the protection of nitrogen, 363 g of 4-amino-3-fluorophenol, 374 g of 4-chloro-N-methylpyridine-2-formamide, and 3740 ml of N, N-dimethyl acetamide are successively added to a reaction vessel, which are stirred to dissolve, and then 115 g of sodium hydroxide is added, the temperature is then raised to 105° C. for 1 hour; 5600 ml of water is added, then cool the mixture to a temperature of 10° C., and stir at the foregoing temperature overnight for crystallization, and then filter and dry to obtain 509 g of a brown colored solid of 4-(4-amino-3-fluorophenoxy)-N-methylpyridine-2-formamide. HPLC content is 99.3%, mp: 141.5 to 142.5° C., yield 88.9%.

EXAMPLE 7

Under the protection of nitrogen, 171.5 g of 4-(4-amino-3-fluorophenoxy)-N-methylpyridine-2-formamide and 1200 ml of acetone are added to a reaction vessel equipped with a stirrer, a thermometer and a dropping funnel, which is kept at 40° C., and then slowly add dropwise 159.5 g of 4-chloro-3-(trifluoromethyl) phenyl isocyanate in 600 ml of acetone solution (completed in about 2 hours), and then maintain the temperature and stir again for another 3 hours, filter to obtain a filter cake, which is then dried in vacuum to obtain 269 g of a white or off-white solid of Regorafenib. HPLC content is 99.4%, mp: 187 to 188° C., yield 85%.

The foregoing are only a few preferred embodiments of the present invention. It should be noted that certain improvements and modifications may be made by those skilled in the art without departing from the principle of the present invention, and such improvements and modifications shall be encompassed within the scope of the present invention.

The invention claimed is:
1. A process for preparing 4-(4-amino-3-fluorophenoxy)-N-methylpyridine-2-formamide shown in the formula below,

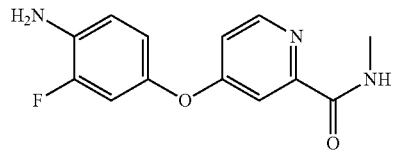 [SMILES: CNC(=O)c1cc(Oc2ccc(N)c(F)c2)ccn1]

wherein the process comprises:
(a) under an inert gas atmosphere, in the presence of an inorganic base, reacting 4-chloro-N-methylpyridine-2-formamide shown in the formula below

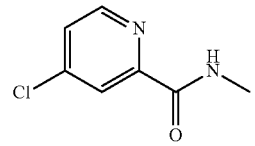

with 4-amino-3-fluorophenol shown in the formula below

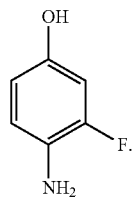

2. The process according to claim 1, wherein the inorganic base is sodium hydroxide or potassium hydroxide.
3. The process according to claim 1, wherein a ratio of 4-chloro-N-methylpyridine-2-formamide, 4-amino-3-fluorophenol and the inorganic base is 1.0: 0.9 to 1.5: 0.9 to 1.5.
4. The process according to claim 1, wherein the reaction is carried out in an organic solvent.
5. The process according to claim 4, wherein the organic solvent is selected from the group consisting of N, N-dimethyl acetamide, N, N-dimethyl formamide and N-methyl pyrrolidone.
6. The process according to claim 1, wherein a reaction temperature of the reaction is from 40 to 160° C.
7. The process according to claim 1, wherein a reaction time for the reaction is from 1 to 24 h.

8. The process according to claim 1, wherein the process further comprises:
(b) after completion of the reaction, adding a suitable amount of water to the reaction solution obtained in step (a), and then cooling to a temperature from −20 to 20° C. for crystallization, so as to obtain 4-(4-amino-3-fluorophenoxy)-N-methylpyridine-2-formamide.

9. The process according to claim 8, wherein a ratio by volume of the water added in step (b) to the reaction solution obtained in step (a) is 0.5 to 3:1.

10. The process according to claim 1, wherein the inorganic base is sodium hydroxide.

11. The process according to claim 1, wherein a ratio of 4-chloro-N-methylpyridine-2-formamide, 4-amino-3-fluorophenol and the inorganic base is 1.0: 1.1 to 1.3: 1.1 to 1.3.

12. The process according to claim 4, wherein the organic solvent is N, N-dimethyl acetamide.

13. The process according to claim 1, wherein a reaction temperature of the reaction is from 80 to 140° C.

14. The process according to claim 1, wherein a reaction temperature of the reaction is from 90 to 110° C.

15. The process according to claim 1, wherein a reaction time for the reaction is from 1 to 6 h.

16. The process according to claim 1, wherein the process further comprises:
(b) after completion of the reaction, adding a suitable amount of water to the reaction solution obtained in step (a), and then cooling to a temperature from 0 to 10° C. for crystallization, so as to obtain 4-(4-amino-3-fluorophenoxy)-N-methylpyridine-2-formamide.

17. The process according to claim 8, wherein a ratio by volume of the water added in step (b) to the reaction solution obtained in step (a) is from 1 to 2: 1.

* * * * *